United States Patent
Thulin et al.

(10) Patent No.: US 9,826,745 B2
(45) Date of Patent: Nov. 28, 2017

(54) METHOD AND A MONITORING SYSTEM FOR MONITORING GAS STUNNING OF BIRDS

(71) Applicant: LINCO FOOD SYSTEMS A/S, Trige (DK)

(72) Inventors: Pernille Thulin, Viborg (DK); Michael Lyngholm, Støvring (DK)

(73) Assignee: Linco Food Systems A/S, Trige (DK)

( * ) Notice: Subject to any disclaimer, the term of this patent is extended or adjusted under 35 U.S.C. 154(b) by 0 days.

(21) Appl. No.: 14/426,206

(22) PCT Filed: Sep. 10, 2013

(86) PCT No.: PCT/DK2013/050289
§ 371 (c)(1),
(2) Date: Mar. 5, 2015

(87) PCT Pub. No.: WO2014/037015
PCT Pub. Date: Mar. 13, 2014

(65) Prior Publication Data
US 2015/0250192 A1   Sep. 10, 2015

(30) Foreign Application Priority Data

Sep. 10, 2012 (DK) .................................. 2012 70552

(51) Int. Cl.
*A22B 3/00* (2006.01)
*A22B 3/08* (2006.01)
(Continued)

(52) U.S. Cl.
CPC .............. *A22B 3/005* (2013.01); *A22B 3/086* (2013.01); *A22B 3/10* (2013.01); *A22B 7/00* (2013.01); *G01N 33/0067* (2013.01); *G06T 7/70* (2017.01)

(58) Field of Classification Search
CPC ........... A22B 3/00; A22B 3/083; A22B 3/005; A22B 3/086
(Continued)

(56) References Cited

U.S. PATENT DOCUMENTS 3,828,396 A * 8/1974 Wernberg ................. A22B 3/00
452/66
6,135,872 A * 10/2000 Freeland .............. A01K 45/005
452/57

(Continued)

FOREIGN PATENT DOCUMENTS

DE   102010036330 B3   7/2010
EP      0441633 A2     8/1991
(Continued)

OTHER PUBLICATIONS

International Search Report for PCT/DK2013/050289, mailed Nov. 22, 2013; ISA/EP.
(Continued)

*Primary Examiner* — Richard Price, Jr.
(74) *Attorney, Agent, or Firm* — Harness, Dickey & Pierce, PLC

(57) ABSTRACT

A method for monitoring gas stunning of birds, where groups of birds are conveyed into and out of a stunning zone (1), and where the concentration of the stunning gas in the stunning zone is measured and adjusted for optimal stunning. The gas concentration is measured at a plurality of measuring positions in the stunning zone and a visual inspection of the birds is performed at two or more of the measuring positions using a visual inspection unit (76), such as a camera, which is moved into the stunning zone together with the group of birds. The groups of birds are advantageously kept in crates (3). The visual inspection unit may be part of a monitoring unit (71) further including a gas sensor (75), said monitoring unit being used for simultaneous (Continued)

measuring of the concentration of the stunning gas and inspection the birds at two or more monitoring positions.

16 Claims, 3 Drawing Sheets

(51) Int. Cl.
  *A22B 3/10* (2006.01)
  *A22B 7/00* (2006.01)
  *G01N 33/00* (2006.01)
  *G06T 7/70* (2017.01)
(58) Field of Classification Search
  USPC .................................................. 452/57, 66
  See application file for complete search history.

(56) References Cited

U.S. PATENT DOCUMENTS

| | | | |
|---|---|---|---|
| 6,174,228 B1* | 1/2001 | Grimsland | A22B 3/00 452/66 |
| 7,097,552 B2 | 8/2006 | Ovesen et al. | |
| 7,438,637 B2 | 10/2008 | Lachariassen et al. | |
| 7,448,943 B1 | 11/2008 | Woodford et al. | |
| 7,717,773 B2 | 5/2010 | Woodford et al. | |
| 2004/0038638 A1* | 2/2004 | Ochten | A22B 1/00 452/66 |
| 2005/0191953 A1* | 9/2005 | Ovesen | A22B 3/00 452/66 |
| 2006/0009142 A1* | 1/2006 | Cattaruzzi | A22B 3/005 452/66 |
| 2006/0135052 A1* | 6/2006 | Horst | A22B 3/086 452/57 |
| 2009/0126647 A1 | 5/2009 | Anderson et al. | |

FOREIGN PATENT DOCUMENTS

| | | |
|---|---|---|
| EP | 0622021 A2 | 11/1994 |
| EP | 1405564 A1 | 4/2004 |
| EP | 2055191 A1 | 5/2009 |
| WO | 9427425 A1 | 12/1994 |
| WO | WO-2004-064528 A1 | 8/2004 |
| WO | 2008127667 A1 | 10/2008 |

OTHER PUBLICATIONS

K. von Holleben et al; Licensing poultry CO2 gas-stunning systems with regard to animal welfare; investigations under ractical conditions; Animal Welfare 2012, V 21(S2): pp. 103-111.

Third Party Observation for Application No. EP20130765637; filed with the EPO by Franco Buzzi, Dec. 21, 2016; Applicant; LINCO Food Systems A/S.

Fruscalzo, Riccardo et al.; "Statement of Defence for LINCO Food Systems A/S," Case No. 18365/2015; Jul. 2015.

Fruscalzo, Riccardo et al.; first Brief; Jul. 2015.

Tornato, Alberto et al.; "I Brief Per Art. 183 VI Paragraph of the Italian Code of Civil Procedure," Maxitech et al v. Linco Food A/S, Case No. 18635/2015; Oct. 2015.

Fruscalzo, Riccardo et al.; "2nd Memorandum Pursuant to Art. 183, VI Paragraph of the Civil Procedure Code for Linco Food Systems A/S," Case No. 18635/2015; Oct. 2015.

Tornato, Alberto et al.; "II Brief Under Art. 183 VI Par. C.P.C. In re Plaintiffs Maxitech and Zanotti," Case No. 18635/2015; Nov. 2015.

Exhibit 30: Email chain between G.R. Webdale (Animal Welfare Control Team) to P. Thurin (inventor) re FAWC advise on LINCO Gas Stunning System, acknowledging slight delay in publication, dated Sep. 11, 2012 and publication of FAWC report therafter.

Fruscalzo, Riccardo et al.; "III Pleadings Pursuant to Art. 183, Par. VI of the Italian Code of Civil Procedure for Linco Food Systems A/S," Case No. 18635/2015; Dec. 2015.

Tornato, Alberto et al.; "3rd Brief Pursuant to Art. 183 Section VI Italian Code of Civil Procedure in re Maxitech and Zanotti," Case No. 18635/2015; Dec. 2015.

Sanchini, Alessandro; "Second Technical Brief in Favour of Linco Food, for the technical evaluation of the Court's Technical Expert Eng. A. Marietti," drafted Jul. 2016.

Buzzi, Franco et al.; "Second Brief Submitted to the Court Expert by the Plaintiffs' Experts," Maxitech et al v. Linco Food A/S, Case No. 18635/2015; Jun. 2016.

Sanchini, Alessandro; "Third Technical Brief in Favour of Linco Food, for the technical evaluation of the Court's Technical Expert Eng. A. Marieffi," drafted Jul. 2016.

Marietti, Andrea; "Relazione peritale preliminare" [Preliminary expert report in Italian]; Tribunale Di Milano, Maxitech SRL v. Linco Food A/S, Case No. 18635/2015; Jan. 2017.

Farm Animal Welfare Committee Guidance to Members (Dec. 2011).

Exhibit 30: Email from G.R. Webdale to P. Thulin re FAWC advise on LINCO Gas Stunning System, acknowledging the publication date of FAWC report will occur after filing of P. Thulin's patent application.

Statement on publication of "FAWC advice on LINCO gas stunning system for poultry," submitted by Richard Aram, FAWC Secretariat, to Gorrissen Federspiel, Jun. 17, 2016.

Shotton, Mark, EIRs/FOI Case Officer; "Request for Information: FAWC Advice on LINCO Gas Stunning System," submitted to Gorrissen Federspiel, Oct. 4, 2016.

Wathes, Christopher, Prof.; "FAWC response to consultations on the implementation of Regulation 1099/2009," Farm Animal Welfare Committee, Oct. 24, 2012.

Email from M. Brookes to V.H. Rosenquist re Question regarding an article from FAWC to Defra Animal Welfare Team Official-Sensitive), Sep. 2, 2016.

Maxitech CO2 Gas Control Panel—Operating Manual and Standard Operating Procedures According to EU Regulation 1099/2009, (rev6) NM 31012013.

Email froM N. Martinelli to . Westh re Faccenda—Technical manula Maxitech CO2 Gas GCP with SOP rev5 NM 17012013, Jan. 17, 2013.

* cited by examiner

METHOD AND A MONITORING SYSTEM FOR MONITORING GAS STUNNING OF BIRDS

CROSS-REFERENCE TO RELATED APPLICATIONS

This application is a 371 U.S. National Stage of International Application No. PCT/DK2013/050289, filed on Sep. 10, 2013, which claims priority to Danish Patent Application No. PA 2012 70552, filed on Sep. 10, 2012. The entire disclosures of the above applications are incorporated herein by reference.

BACKGROUND OF THE INVENTION

The present invention relates to a method for monitoring gas stunning of birds, where groups of birds are conveyed into and out of a stunning zone, and where the concentration of the stunning gas in the stunning zone is measured and adjusted for optimal stunning, and to a monitoring system.

The applicant's prior patent application EP1405564A1 discloses a gas stunning system intended for poultry, where the stunning is optimized in respect of capacity, the size and number of birds in each group and the physical condition of the birds, which again depends on factors such as temperature, transport time and waiting time in the slaughterhouse. This optimization is achieved by shortening or prolonging the conveying time and/or the conveying route through the stunning zone if the birds are not properly stunned when coming out of the stunning zone.

Introducing the system known from EP1405564A1 has made the slaughtering process more efficient, since the number of birds which are killed prematurely due to excessive stunning has been minimized, and has also contributed considerably to the welfare of the birds.

BRIEF SUMMARY OF THE INVENTION

The process of optimizing animal welfare, however, is ongoing and it therefore the object of the invention to provide a method and a system, which allow the stunning process to be optimized even further with respect to ensuring that each bird is stunned with a minimum of discomfort.

This is achieved with a method where the concentration of the gas is measured at a plurality of measuring positions in the stunning zone, where a visual inspection of the birds is performed at two or more of the measuring positions, and where a visual inspection unit is moved into the stunning zone together with a group of birds and used for the visual inspection of the birds in this group. A monitoring system comprising one or more gas sensors adapted for measuring the gas concentration at a plurality of measuring positions in the stunning zone and one or more visual inspection units adapted for inspecting the birds at two or more of the measuring positions, may be used for this purpose, one or more of the visual inspection units being adapted for being moved into the stunning zone together with a group of birds.

Performing an inspection in the stunning zone allows an immediate adjustment of the stunning conditions, i.e. the gas concentration, conveying speed and/or conveying path, if the birds display a behaviour associated with the stunning being either too heavy or too light. Compared to the known methods, where the inspection of the birds is not performed systematically until the birds have left the stunning zone and where the adjustment is therefore delayed corresponding to the time of travel through the system, this means that the number of birds exposed to non-optimal stunning conditions is reduced. The invention is particularly advantageous when the stunning zone includes a stunning pit, where it is normally not possible to provide inspection windows allowing manual inspection at the levels with the highest gas concentrations.

Moreover, the inspection at two or more places in the stunning zone combined with measurements of the gas concentration at the same places allows a much higher accuracy in the determination of the effect of the stunning. Previously the focus have being primarily on the end result, i.e. if the birds coming out of the stunning zone are unconscious but still alive. Now it is also possible to monitor the reactions of birds during the process to discover if the birds feel discomfort due to the exposure to the stunning gas being either too rapid or too slow. The result of the inspection of the reaction of the birds combined with the measurement of the gas concentration at several places in the stunning zone can thus be used for further adjustment of the stunning process.

Still another advantage of the combined measurement of gas concentration and inspection of the reactions of the birds is that the stunning process can be documented by simply storing these data. This makes it possible to live up to the still stricter regulatory requirements on animal welfare, which are being implemented in countries all over the world. As an example European regulations prescribe that when stunning poultry using carbon dioxide, the birds must be unconscious before reaching zones with a gas concentration of 40% or more. Compliance with these regulations can be documented by performing the visual inspection at two measuring positions; one above the 40% limit and one below it.

It is noted that the measuring positions does not have to be predetermined corresponding to specific levels or positions in the stunning zone but may be adjusted, when the stunning conditions are adjusted. By using a movable gas sensor and/or multiple gas sensors it is even possible to provide a mapping of the gas concentration over the extent of the stunning zone.

In many gas stunning systems intended for birds, for example the one described in EP1405564A1, the conveying of the birds is stopped as a part of the stunning process at two or more predetermined levels when being conveyed into the stunning zone and it may then be advantageous to measure the concentration of the stunning gas at each of these levels. Such systems typically include 5-6 levels and the visual inspection can then be performed for example at the last three levels, where the gas concentration is highest.

To avoid unnecessary handling of the birds, which will result in raised stress levels, and reduce the risk of damages to the wings, it preferred to keep the birds in crates, which may advantageously be the crates used for transporting the birds from the farm to the slaughterhouse. The conveyor should then be adapted for receiving such crates and conveying them through the stunning zone, but it is also possible to provide crates on the conveyor and to load the birds into these crates shortly before stunning.

With the transport crates most commonly used in poultry slaughterhouses today the best view of the birds are from the top and the visual inspection unit is therefore advantageously arranged at or slightly above the upper edge of the crate when in operation. The optimal position of the gas sensor may, however, be different, for example to prevent it from blocking the view of the visual inspection unit or minimizing the risk of the visual inspection unit disturbing the gas. The gas sensor and the visual inspection unit may therefore be somewhat offset. Accordingly, the term "measuring position" should not be understood as an exact point, but may be an area of limited size compared to the distance between the levels in the stunning zone.

The visual inspection unit may in principle be any, which allows an inspection of the condition of the birds, but it is presently considered advantageous to use an analogue and/or digital imaging reproduction unit, which may be connected to a central processing unit and allows an operator or control program to easily determine any movements of the birds. If any undesired movement is detected, the operator or control program may use these data for initiating an adjustment of the stunning process.

Video sequences may be used, but it is also possible to use still images of the birds, in which case a comparison between two or more images taken with a short time interval may be used for determining if any of the birds are moving.

In one embodiment of the invention, the visual inspection unit is moved into the stunning zone together with a group of birds and used for visual inspection of the birds in this group at two or more monitoring positions. This allows the monitoring to be performed using only a single camera or like visual inspection unit and for an easy adjustment of the position of the visual inspection unit, when the stunning process is adjusted. The term "monitoring position" is used in order to distinguish those measuring positions, where a visual inspection is performed from those where only the gas concentration is measured. Again it is to be understood that the term "position" is to be interpreted broadly so that visual inspection unit and the gas sensor does not have to be located at the exact same point but may be somewhat apart to allow optimal monitoring as long as they are associated with the same level in the stunning zone. Likewise it is to be understood that the term "level" not only includes different depths in a stunning pit, but also different places in stunning zones where the birds are conveyed following horizontal or inclined paths.

As described for the visual inspection unit, a gas sensor may also be adapted for being moved within the stunning zone and for performing two or more measurement associated with the same group of birds as it is conveyed into the stunning zone.

In an advantageous embodiment the visual inspection unit and gas sensor are part of a monitoring unit, said monitoring unit being used for simultaneous measuring of the concentration of the stunning gas and inspection of the birds. The visual inspection unit may in principle be a camera running constantly and thus allowing a continuous inspection of the birds in a group and the same applies to the gas sensor. For practical reasons it may, however, be preferred to only collect data from the gas sensor and/or visual inspection unit at intervals.

Using a monitoring unit has the further advantage that in the event of malfunction, the entire unit may be driven out of the stunning zone and replaced without having to interrupt the stunning process as would be the case if visual inspection units and/or gas sensors were fixedly mounted in the stunning zone. This is particularly advantageous when the stunning zone is a stunning pit, where there is usually no access from the sides and where maintenance and repair inside the stunning zone can therefore only be undertaken by descending into pit.

The monitoring system preferably comprises a central processing unit receiving measuring and inspection signals from the gas sensor(s) and visual inspection unit(s), respectively. Based on these signals the central processing unit presents system status information to an operator and/or calculates the needed adjustment to the stunning process. For this purpose the central processing unit, which is preferably a computer, is advantageously equipped to perform image recognition and processing. The process may even be fully automatic, so that the central processing unit automatically generates control signals to the gas stunning system based on the signals received from the gas sensor(s) and visual inspection unit(s).

The method and system according to the invention has been developed for use in poultry slaughterhouses, but it will be understood that they may also be used for stunning other types of birds. Certain parameters such as the time in the stunning zone and the nature of any crates used will of course have to be adapted accordingly, but this will be easily done by a skilled person.

Carbon dioxide is currently preferred as the stunning gas, but other asphyxiant gasses such as argon or nitrogen as well as mixtures of two or three of these gasses may also be used. In the following reference will be made only to carbon dioxide but unless otherwise stated it is to be understood that other gasses and gas mixtures may also be employed.

In the following the invention will be described in closer detail with reference to the drawing, where:

BRIEF DESCRIPTION OF THE SEVERAL VIEWS OF THE DRAWING(S)

DETAILED DESCRIPTION OF THE INVENTION

Figure 1:
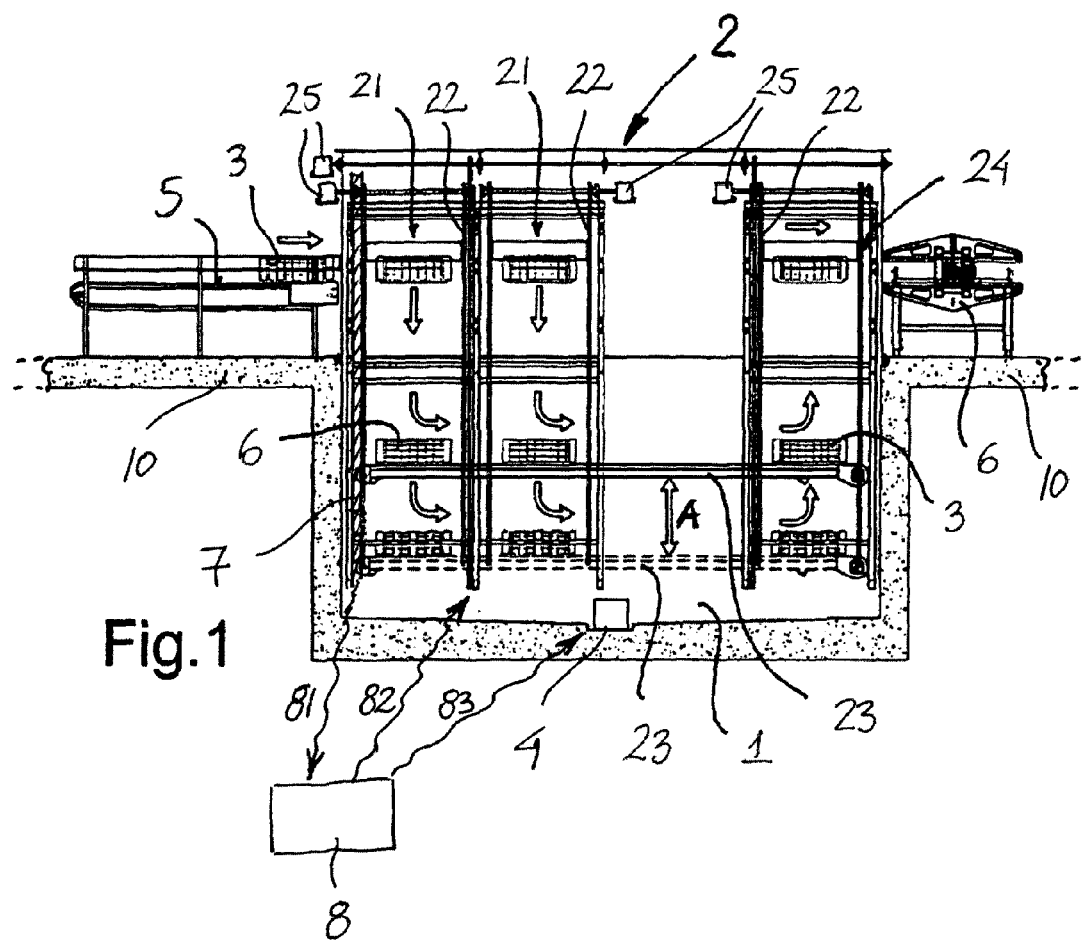
FIG. 1 is a sketch of a system for gas stunning poultry.

A gas stunning system is shown in FIG. 1. It includes a stunning zone in the form of a stunning pit 1 and a conveyor system 2 carrying crates 3 each holding a group of birds into and out of the pit as indicated by the arrows. Gas is supplied to the pit via a gas supply system 4, which is not shown in detail but known to the skilled person.

Crates 3 are supplied to the stunning system via a supply conveyor 5 and after stunning they are delivered to a crate turning unit 6, which is used for emptying the crates. Both the supply conveyor and crate turning unit are well known to the skilled person and will therefore not be described in closer detail here.

Unnecessary handling of the birds should be avoided and when stunning poultry it is therefore preferred to keep the birds in the transport crates used for transporting them from the farm to the slaughterhouse. In the drawing the stunning system 2 is shown with such poultry transport crates 3 and the following description will be based on the stunning of poultry, but it is to be understood that similar systems may also be used for stunning other birds. Likewise it will be understood that when in the following reference is may to birds in crates this is only one example of an easy and well proven way of keeping groups of birds, but that the crates are not absolutely necessary.

If not using transport crates as shown in FIG. 1, the supply conveyor 5 and the crate turning unit 6 may be embodied differently or even left out, but means should then be provided for getting the stunned birds out of the stunning zone and/or off the conveyor.

A stunning pit 1 is typically a concrete covered hollow in the floor 10 of the slaughterhouse as shown in FIG. 1, but may also be embodied as a closed structure arranged on top of the floor. Using a hollow has the advantages that it is not necessary to lift the birds to get them into the pit and that since carbon dioxide is heavier than ambient air it will be contained and thus does not constitute a serious work environment issue. One alternative to the stunning pit is a stunning tunnel where the concentration of the stunning gas varies over its length so that different sections of the tunnel constitutes different levels in the stunning zone. Another alternative is a series of stunning chambers with different gas concentrations arranged in continuation of each other.

The stunning gas may be heated to ensure that the temperature within the stunning zone 1 is maintained at approximately the same level as in the rest of the slaughterhouse. When using a pit, the gas is injected at the base of the pit and fans or injection of compressed air (not shown) may be used to regulate the gas concentration in different parts of the pit. That is to make sure that the gas is distributed to all areas of the pit and possibly to compensate for the agitation caused by the movement of crates 3, which will induce a counter-clockwise movement when seen from the direction in FIG. 1.

Figure 2:
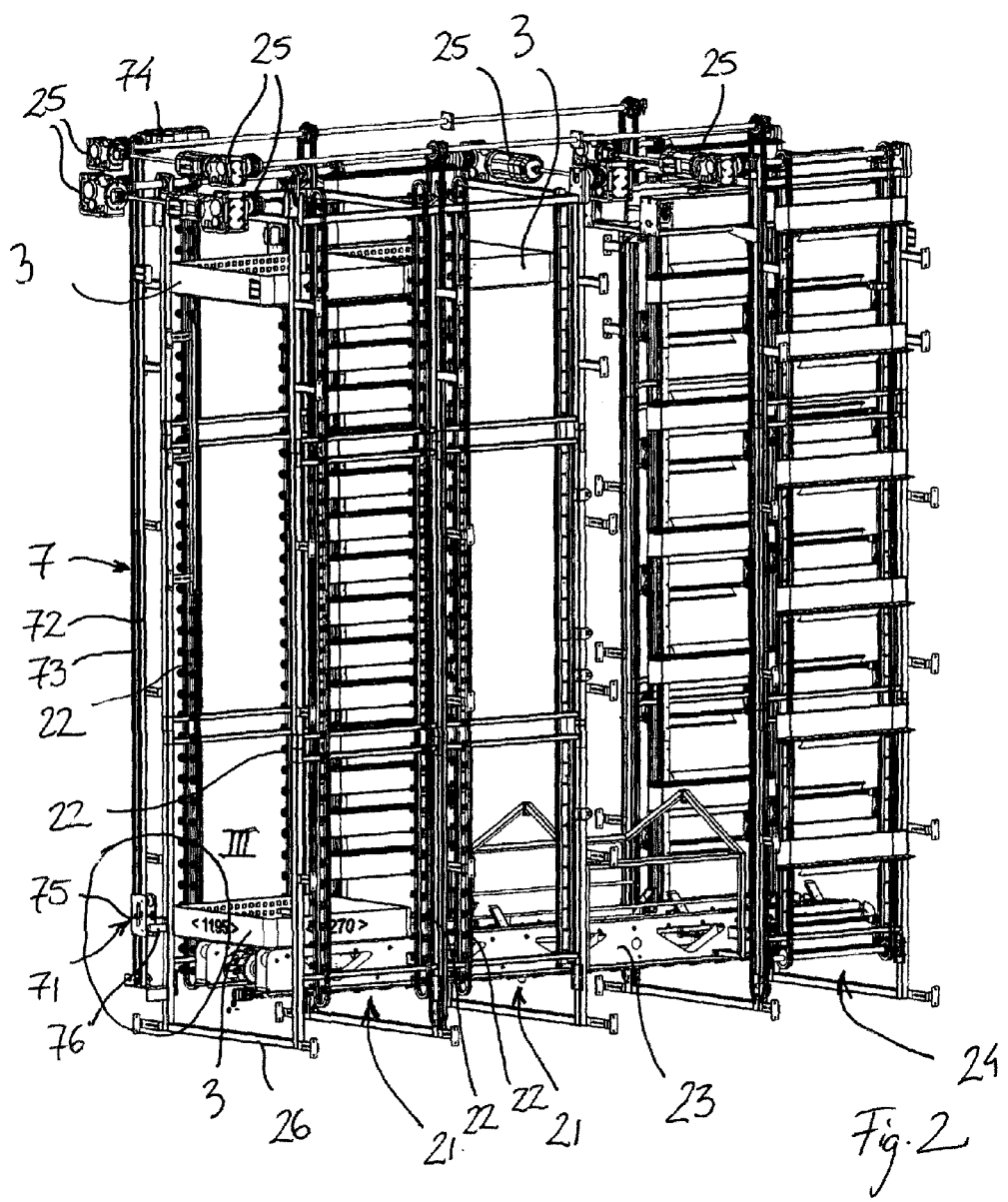
FIG. 2 is a perspective view of the conveyor system in FIG. 1 mounted with a monitoring system according to the invention.

From the supply conveyor 5 the crates 3 are successively conveyed into a vertical downwards conveyor 21, which, as may also be seen in FIG. 2, is driven by endless chain conveyors 22. When reaching the lowermost level of the conveyor system the crates 3 are transferred to a horizontal conveyor 23, which takes them over to the opposite side of the pit, where they are transferred to a vertical upwards conveyor 24. The conveyors and the motors 25 driving them are preferably mounted on a common rack 26 and for safety reasons a covering (not shown) is applied on the part of the conveyor system projecting above the floor 10.

As indicated by the double-arrow A in FIG. 1 the horizontal conveyor 23, which defines the lowermost level of the conveyor system, may be raised in relation to the bottom of the pit 1 from the position shown in punctured lines to the position shown in full lines. In this way the conveying route through the pit may be adjusted as described in more detail in EP1405564A1 in order to adjust the stunning process.

The conveyor system described herein is only to be regarded as an example of how the groups of birds, which are advantageously arranged in crates, can be conveyed through a stunning zone. The invention is not limited to any particular design of the conveyor system as long as means are provided for taking the birds through the stunning zone.

As indicated in FIG. 1 and seen more clearly in FIG. 2 a monitoring system 7 is mounted at the side of the conveyor system and extending over substantially the entire height of the stunning pit 1. Only one such system 7 is shown in the drawing but it is to be understood that more may be present for increased flexibility, for example that a similar system may be found at both of the downwards conveyors 21 shown in FIGS. 1 and 2.

Figure 3:
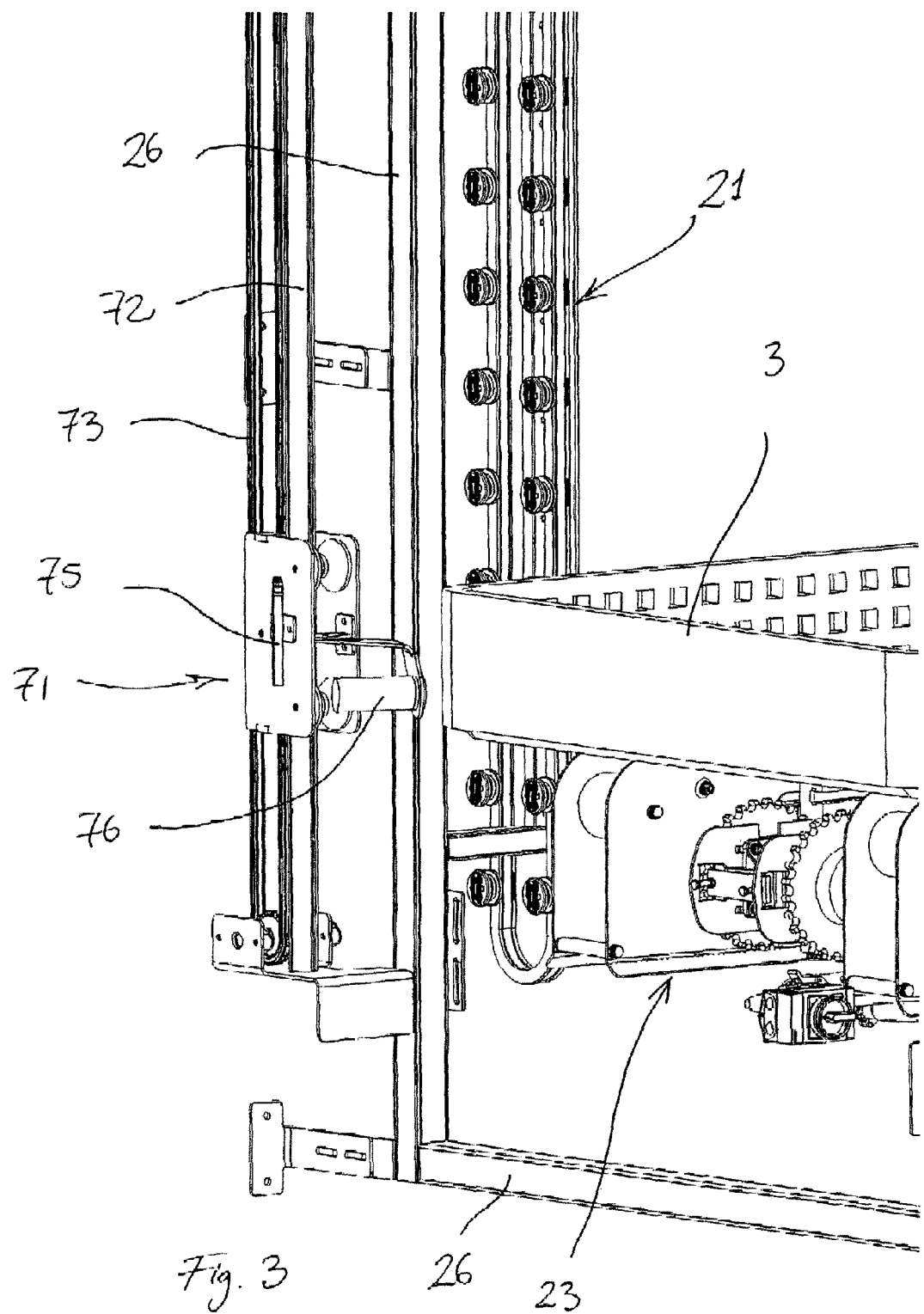
FIG. 3 is an enlarged view of the detail marked III in FIG. 2.

The monitoring system 7 comprises a monitoring unit 71 mounted to run up and down a rail 72 driven by a belt drive 73 with a motor 74 as shown in FIGS. 2 and 3. The monitoring unit includes a gas sensor 75 and a visual inspection unit 76, here in the form of a digital video camera. It is further possible to provide the monitoring unit with a light source (not shown) or other additional equipment needed for achieving usable images and reliable gas concentration measurements.

Power cables and data transmission cables are not shown in the drawing but may be present. Alternatively the gas sensor and visual inspection unit may be battery powered or the rail may comprise electrically conducting material. Data from the sensor and inspection unit may also be transmitted via cables or via wireless connections as will be explained later.

When crates 3 are conveyed into the pit 1 by means of the vertical downward conveyor 21, they are stopped a predetermined levels with ever increasing gas concentrations, starting at a low gas concentration of approximately 2% and ending at a concentration of no more than 50% at the bottom of the pit. When the levels are arrange with substantially equal distance, intermediate levels will typically be located in zones having gas concentrations of 15%, 25%, 35% and 40%. This division of the pit into zones of different gas concentrations comes naturally when carbon dioxide is injected at the bottom of the pit, but may of course be controlled or adjusted, for example by means of fans or the injection of compressed air or gas.

It is noted that the monitoring of the stunning process does not necessarily involve a gas concentration measurement and visual inspection at all levels. As an example the gas distribution in a stunning pit is usually relatively stable once the system is running and measuring the gas at every other level will therefore give a relatively accurate picture of the gas concentration at all levels. Likewise, the visual inspection can be performed only at levels, where the birds are expected to display certain behaviours, which may be used as an indicator of the effectiveness of the stunning process. A monitoring of the birds, i.e. both a measuring of the gas concentration and a visual inspection, should, however, be performed at least at two levels.

The stop at each level will automatically make the birds lift their heads. When they do so, their heads will come up into a zone having a slightly lower gas concentration, giving them the feeling of breathing relatively freely. This calming effect prevents the birds from becoming too stressed and the risk of injuries is thus minimized. It is, however, to be understood that the birds may also be conveyed in a continuous motion without stops, simply passing slowly through the different concentration zones.

Typically the lowering into a pit takes a total of 5 minutes, whereas the raising of the crate, when the birds are unconscious takes only 1 minute. These time periods may of course vary, but as the heart of a chicken will only continue to beat for approximately 4 minutes after stunning, the raising of the crates out of the pit has to be relative quick. Optimally poultry is killed approximately 1½ minute after stunning. Similar time intervals apply in stunning zones of other designs and when not using crates.

The dwell time at each level need not be the same. On the contrary it may be expedient to keep the birds at the levels with low gas concentration only for as long as it takes them to calm down, whereas they are kept longer at the levels with a relatively high gas concentration to ensure a proper stunning. Typically the dwell time at the first level will be approximately half of that at the last level.

It is generally accepted that to maintain acceptable animal welfare all individuals must have lost consciousness before being exposed to a carbon dioxide concentration of 40% or more. The monitoring system 7 ensures that this is always respected by measuring of the gas concentration and at the same time performing a visual inspection of the birds. If a carbon dioxide concentration of 40% or more is measured by the gas sensor 75 and the visual inspection unit 76 at the same time detects signs of birds still being conscious, the stunning process can be adjusted immediately by pro-longing the dwell time and/or by adjusting the distribution of the gas in the pit.

In the embodiment shown in FIGS. 2 and 3, the monitoring unit 71 is arranged to run on a rail 72 along the vertical conveyor 21, which makes it possible to follow a particular crate or group of birds on its way down into the pit. In this way it is possible to record a video showing the reactions of the birds and a coupled set of data showing the gas concentration. During normal operation of the stunning system it will, however, be expedient to measure the gas concentration only at predetermined measuring positions, preferably one at each level, and to only have still images or shorter video sequences from measuring positions at levels with gas concentrations just below and just above 40% carbon dioxide to document that the stunning process is according to plan. A similar monitoring unit running on a horizontal or inclined rail (not shown) may be used where the stunning zone is a tunnel or a series of chambers and will be operated in substantially the same way.

The measuring data and images or video sequences are sent to a computer 8 serving as the central processing unit as indicated by the arrow 81 in FIG. 1. This computer may display potential problems to an operator (not shown), who will decide on the need for adjustment of the system. For this purpose the computer is programmed with image recognition and processing software allowing it to distinguish signs of the birds being conscious from the epileptic movement often displayed by unconscious birds. In one embodiment, two images taken with an interval of approximately one second is compared and if there are any differences, a video sequence is shown to the operator for evaluation. More sophisticated image processing programs will, however, be capable of making this evaluation automatically and to generate control signals 82, 83 for the system(s) controlling the gas injection 4 and/or conveyors 21,22,23,24, respectively.

As an alternative to the image recordation and processing described above it is also possible to use a movement detector (not shown) as the visual inspection unit, in which case a threshold value for the acceptable amount of movement could be set for each of the monitoring positions.

In FIG. 1 the signals sent to and from the central processing unit 8 are shown as wireless signals. The design and function of the central processing unit and its communication with other parts of the stunning system will to some degree depend on the type of sensors and visual inspection unit(s), but is independent of the type stunning zone, conveyors and crates used.

In the embodiment in FIGS. 2 and 3 the gas sensor 75 and visual inspection unit 76 are shown as being arranged at substantially the same height, which ensures very precise measurements of the gas concentration at the level, where the visual inspection is performed. It may, however, be expedient to arrange them further apart, for instance to compensate for the stirring of the gas caused by the downwards movement of the crate. Moreover, to allow the visual inspection unit to inspect all of the birds in the crate, it may need to be located somewhat higher in relation to the crate than shown in FIGS. 2 and 3 and it may also be advantageous to angle the visual inspection unit.

In the embodiment described with reference to the drawing, the gas sensor 75 and visual inspection unit 76 are integrated parts of the monitoring unit 71, but it is also possible to provide the gas sensors at fixed positions in the pit. Such embodiments, however, involve the use of more sensors and hence make the total system more expensive. Another advantage of using an integrated unit is that in the event of malfunction, the monitoring unit can be driven to the top of the rail 72 and replaced by a spare unit with virtually no down-time. If using fixed sensors the pit will have to be emptied before repair and maintenance work can be performed. It is of course also possible to provide the gas sensor 75 and visual inspection unit 76 as separate moveable units running independently, for example one on each side of the rail 72.

In an alternative embodiment a monitoring unit is mounted on a chain conveyor 22 used for driving the birds into the pit and thus follows the crate or group of birds transported on one particular position of the downwards conveyor 21. This minimizes the number of components of the system, but also involves a decreased flexibility of the system, as only birds at a certain position on the conveyor can be monitored and as the conveyor will have to perform a full cycle before a new monitoring sequence can be initiated. These downsides may, however, be compensated for by using two or more monitoring unit on each conveyor. It is also possible to provide either the gas sensor or the visual inspection unit as a separate system and have the other mounted on the conveyor.

Above the invention has been described with reference to embodiments with chain conveyors, but it will be understood that conveyors may also be driven for example by belts or hydraulics in stead of chains.

If wishing for an even more precise control of the gas stunning system, a monitoring unit, gas sensor and/or visual inspection unit may also be provided on or at the upwards conveyor 24. This will for example allow an inspection of the epileptic movements often displayed by stunned birds to see if they follow the expected pattern.

The invention claimed is:

1. A method for monitoring gas stunning of birds, where groups of birds are conveyed into and out of a stunning zone, and where the concentration of the stunning gas in the stunning zone is measured and adjusted for optimal stunning,
wherein
the concentration of the gas is measured at a plurality of measuring positions in the stunning zone, that a visual inspection of the birds is performed at two or more of the measuring positions, and that a visual inspection unit is moved into the stunning zone together with a group of birds and used for the visual inspection of the birds in this group.

2. The method according to claim 1, where the groups of birds are kept in crates, where the crates are conveyed into and out of a stunning zone, and where the visual inspection unit is moved into the stunning zone together with a crate.

3. The method according to claim 1, where the conveying of the birds into the stunning zone is stopped as a part of the stunning process at two or more predetermined levels and that the concentration of the stunning gas is measured at each of these levels.

4. The method according to claim 1, where the visual inspection unit is an analogue and/or digital imaging reproduction unit.

5. The method according to claim 1, where the visual inspection unit is part of a monitoring unit further including a gas sensor, said monitoring unit being used for simultaneous measuring of the concentration of the stunning gas and inspection of the birds.

6. The method according to claim 1, where a central processing unit receives measuring and inspection signals from the gas sensor(s) and visual inspection unit(s), respectively, and where the central processing unit presents system status information to an operator and/or calculates the needed adjustment to the stunning process based on the measuring and inspection signals.

7. The method according to claim 6, where the central processing unit automatically generates control signals to the gas stunning system based on the measuring and inspection signals.

8. The method according to claim 1, where the stunning gas is carbon dioxide and where the visual inspection is performed at a first monitoring position where the concentration of the stunning gas is below 40% and at a second monitoring position where the concentration of the stunning gas is above 40%.

9. The method according to claim 1, where the stunning zone includes a stunning pit.

10. A monitoring system for monitoring gas stunning of birds, where groups of birds are conveyed into and out of a stunning zone, comprising at least one gas sensor and a visual inspection unit,
wherein
the gas sensor(s) is/are, adapted for measuring the gas concentration at a plurality of measuring positions in the stunning zone, that one or more visual inspection unit(s) is/are adapted for inspecting the birds at two or more of the measuring positions, and that one or more of the visual inspection unit(s) is/are adapted for being moved into the stunning zone together with a group of birds.

11. The monitoring system according to claim 10, where the groups of birds are kept in crates and where the visual inspection unit is adapted for moving into the stunning zone together with a crate.

12. The monitoring system according to claim 10, where the visual inspection unit is an analogue and/or digital imaging reproduction unit.

13. The monitoring system according to claim 10, further comprising a central processing unit receiving measuring and inspection signals from the gas sensor(s) and visual inspection unit(s), respectively.

14. The system for gas stunning of birds including a stunning zone, a conveyor system for conveying groups of birds into and out of the stunning zone and a monitoring system according to claim 10.

15. The system according to claim 14, where the conveyor system is adapted for conveying crates containing birds.

16. The system according to claim 14, where the stunning zone includes a stunning pit.

* * * * *